(12) United States Patent
Shuber

(10) Patent No.: US 8,575,124 B2
(45) Date of Patent: Nov. 5, 2013

(54) COMPOSITIONS AND METHODS FOR TREATING CANCER

(75) Inventor: Anthony P. Shuber, Mendon, MA (US)

(73) Assignee: Anthony P. Shuber, Mendon, MA (US)

( * ) Notice: Subject to any disclaimer, the term of this patent is extended or adjusted under 35 U.S.C. 154(b) by 215 days.

(21) Appl. No.: 13/030,989

(22) Filed: Feb. 18, 2011

(65) Prior Publication Data

US 2011/0200621 A1 Aug. 18, 2011

Related U.S. Application Data

(60) Provisional application No. 61/305,836, filed on Feb. 18, 2010.

(51) Int. Cl.
*C12N 15/11* (2006.01)
*C07H 21/04* (2006.01)

(52) U.S. Cl.
USPC ........................................ 514/44 R; 536/24.3

(58) Field of Classification Search
None
See application file for complete search history.

(56) References Cited

U.S. PATENT DOCUMENTS

| | | | | |
|---|---|---|---|---|
| 5,391,723 A | * | 2/1995 | Priest | 536/23.1 |
| 7,846,436 B2 | * | 12/2010 | Srivastava et al. | 424/133.1 |
| 2006/0013860 A1 | * | 1/2006 | Ng et al. | 424/435 |

OTHER PUBLICATIONS

Liang et al (Cancer research, 2005, 65:967-971).*
Yoon et al (American Journal of Pathology, 2002, 161:391-397).*

* cited by examiner

*Primary Examiner* — Laura B Goddard
(74) *Attorney, Agent, or Firm* — Thomas C. Meyers; Brown Rudnick LLP

(57) ABSTRACT

This invention generally relates to compositions and methods for targeted delivery of chemotherapeutic agents to cancerous and pre-cancerous cells, thereby treating a cancer in a subject.

14 Claims, No Drawings

COMPOSITIONS AND METHODS FOR TREATING CANCER

RELATED APPLICATION

This application claims priority to provisional application Ser. No. 61/305,836, filed on Feb. 18, 2010, the entirety of which is incorporated by reference herein.

FIELD OF THE INVENTION

This invention generally relates to compositions and methods for targeted delivery of chemotherapeutic agents to cancerous and pre-cancerous cells, thereby treating a cancer in a subject.

BACKGROUND

A variety of therapies are available for treatment of cancer in a subject, including drug treatment therapy, radiation therapy, surgery, and alternative therapies. These therapies act by killing cells of the body that divide rapidly, such as cancerous cells, but also normal cells such as hair follicles, cells of the digestive tract, and bone marrow. Thus a problem with those therapies is that they are non-specific for targeting a cancerous cell, i.e. the therapy kills normal and cancerous cells. While killing the cancerous cells, collateral damage and death to the normal cells results in other deleterious effects to the patient, e.g., loss of hair, blood disorders such as leucopenia and thrombocytopenia, digestive disorders, and physical pain.

There is a need for compositions and methods that specifically target cancerous and pre-cancerous cells in a subject, while not killing the normal cells of the body.

SUMMARY

This invention generally relates to compositions and methods for targeted delivery of chemotherapeutic agents to cancerous and pre-cancerous cells, thereby treating a cancer in a subject. Cancers typically result from genomic instability. That is, a disruption in genomic stability, such as a mutation, that has been linked to the onset or progression of a cancer. A typical mutation event that gives rise to a cancer or a pre-cancerous cell is a loss of genetic material from a wild-type sequence, e.g., a deletion event. Thus a mutated sequence from a cancerous or pre-cancerous cell from a subject is typically missing a region of genomic material compared to a wild-type sequence from a normal cell. Methods of the invention take advantage of those sequence differences between a subject's normal cells and those that are cancerous or pre-cancerous for treatment of cancer in the subject by specifically targeting and killing the diseased cells.

Methods of the invention involve introducing a cytotoxic element that induces cell death in cells having genomic instability, but that is inert in wild-type cells. The invention provides compositions and methods that selectively target genomic instability and, thus, selectively target cancer cells. Compositions according to the invention selectively kill cancer cells while not damaging healthy cells (i.e., cells that do not contain a genomic instability). As a result, side effects of treatment are significantly reduced, along with a reduction in the impairment of normal tissue function. A preferred composition of the invention comprises a cytotoxic element that induces cell death in genomically-unstable cells, but that does not kill healthy cells. For example, an exemplary composition of the invention comprises nucleic acids that hybridize to adjacent target regions in a genomically unstable cells, wherein the target regions are separated from each other in a healthy cells. By way of example, a composition of the invention comprises two nucleic acid probes that hybridize to two separate regions of a cell's genomic DNA that are distant from one another in a healthy cell. One of the probes contains a cytotoxic agent and the other contains an activator of the cytotoxic agent. The activator activates the cytotoxic agent only when the two probes hybridize to regions of the genome that are within proximity sufficient for the activation to occur. The probes are designed to 1) hybridize to regions of the target genome that are separated in a healthy cell by a distance that is too great for the activator to induce the cytotoxic agent upon hybridization of the probes and 2) hybridize to regions that are sufficiently close for cytotoxic activation in a cell that is genomically-unstable. The design of the probes is preferably, but not necessarily, driven by sequencing nucleic acid in cancer cells (e.g., cells from a biopsy) to determine where genomic instability (e.g., a deletion) has occurred. In other embodiments, the cytotoxic agent is a nucleic acid itself that, when present in proximity of a second nucleic acid induces cell death.

The invention also contemplates methods comprising administering a first nucleic acid probe and a second nucleic acid probe to a subject. A first probe comprises a cytotoxic agent and the second probe comprises an activator of the cytotoxic agent. For example, an activating agent is attached to the first probe, and a prodrug of a chemotherapeutic agent is attached to a second drug. The probes are designed to hybridize to first and second sequence portions that are identical in the wild-type sequence and the mutated sequence. The first and second portions flank the region of genetic material that is lost from a wild-type sequence to result in the mutated sequence present in the cancerous and pre-cancerous cells. Thus, the probes are brought into proximity for activation of the therapeutic agent only when there is a loss of genomic material. While the probes can hybridize to contiguous regions in the mutated cells, all that is required is that they hybridize in sufficient proximity for activation of the cytotoxic agent in the mutated cells (but are out of proximity for activation in a healthy cell).

Upon administration of the probes to a subject, the first and second probes hybridize to the first and second portions of the sequences in the normal cells and in the cancerous or pre-cancerous cells. For the wild-type sequences, the first and second portions are not within sufficient proximity of each other for the activating agent to convert the prodrug to an active form of the chemotherapeutic agent. Thus the chemotherapeutic agent remains inactive and the normal cell is unharmed.

However, the sequences in the cancerous or pre-cancerous cells have undergone a mutation resulting in loss of a certain amount of genetic material between the first and second portions. Thus in the mutated sequences, the first and second portions are within sufficient proximity of each other for the activating agent to convert the prodrug to an active form of the chemotherapeutic agent, thereby providing targeted delivery of the chemotherapeutic agent to the cancerous or pre-cancerous cell in the subject, and killing those cells.

One aspect of the invention provides a method of treating a cancer including administering to a subject a prodrug of a chemotherapeutic agent, coupled to a first nucleic acid probe, and administering an activating agent, coupled to a second nucleic acid probe, in which the probes hybridize to a first sequence portion and a second sequence portion that are identical in both a wild-type sequence found in a normal cell of the subject and a mutated sequence found in a cancerous or pre-cancerous cell of the subject. In the wild-type sequence, the first and second portions are not within sufficient proximity to each other for the activating agent to convert the prodrug to an active form of the chemotherapeutic agent. In the mutated sequence, the first and second portions are within sufficient proximity to each other for the activating agent to convert the prodrug to an active form of the chemotherapeutic agent, thereby providing targeted delivery of the chemotherapeutic agent to the cancerous or pre-cancerous cell in the subject.

Differences in sequences may be determined by many methods, such as sequencing. Sequencing may be by a chain-termination sequencing technique (Sanger sequencing) or by a single molecule sequencing-by-synthesis technique. In certain embodiments, a nucleic acid is obtained from the normal cell of the subject and sequenced, thereby acquiring a wild-type sequence. Also, a nucleic acid is obtained from the cancerous or pre-cancerous cell of the same subject and sequenced, thereby acquiring a mutated sequence. Once the two different sequences are acquired, the wild-type sequence and the mutated sequences are compared, and thus a determination of the difference between the wild-type sequence and the mutated sequence is made. The difference between the wild-type sequence and the mutated sequence is the mutated region to which the nucleic acid probes will be designed to flank. In certain embodiments, the difference between the wild-type sequence and the mutated sequence is the result of a loss of genetic material between the first and second portions in the mutated sequence, in which the loss of genetic material results from a mutation event including a deletion, a substitution, or a rearrangement.

The first and second nucleic acid probes hybridize on the mutated sequence and flank the mutated region. One probe hybridizes upstream of the mutation while the other probe hybridizes downstream of the mutation. In certain embodiments, once administered, the first and second probes hybridize adjacent to each other on the mutated sequence. Alternatively, the first and second probes may hybridize to the mutated sequence with a region of the mutated sequence remaining between the first and second probes. In certain embodiments, the administration of the first and second probe may be sequential. Alternatively the administration of the first and second probes may be simultaneous or separate. In another embodiment, the probe is a DNA probe.

Probe lengths are known in the art and synthesizing probes of any length is well within one of skill in the art. Probe lengths are based on the genetic sequences of the subject. Exemplary probe lengths range from about a 15-mer to about a 25-mer. The probes do not have to be of the same length. In certain embodiments, the probes are the same length, while in other embodiments, the probes are of different lengths. The nucleic acid probes may couple to the prodrug or activating agent by either a covalent linkage or alternatively a non-covalent linkage.

Exemplary chemotherapeutic agents that are administered in the form of a prodrug include altretamine, asparaginase, bleomycin, capecitabine, carboplatin, carmustine, cladribine, cisplatin, cyclophosphamide, cytarabine, dacarbazine, actinomycin D, docetaxel, doxorubicin, imatinib, etoposide, fludarabine, fluorouracil, gemcitabine, hydroxyurea, idarubicin, ifosfamide, irinotecan, methotrexate, mitomycin, mitotane, mitoxantrone, paclitaxel, topotecan, vinblastine, vincristine, and vinorelbine. Exemplary activating agents include a chemically conjugated antibody fragment, a metabolizing enzyme, and a catalytic antibody.

The method of the invention may be used to treat any cancer. Exemplary cancers include brain, bladder, blood, bone, breast, cervical, colorectal, gastrointestinal, endocrine, kidney, liver, lung, ovarian, pancreatic, prostate, and thyroid.

Another aspect of the invention provides a method of treating a cancer in a subject including sequencing a nucleic acid found in a normal cell of a subject to obtain a wild-type sequence. The method further involves sequencing a nucleic acid found in a cancerous or pre-cancerous cell of the same subject, to obtain a mutated sequence of the cancerous or pre-cancerous cell of the subject. Once both sequences have been obtained, the wild-type sequence and the mutated sequence are compared which results in a determination of the difference between the two sequences, correlating to the difference in sequences between a normal cell and a cancerous or pre-cancerous cell of the subject.

After determining the difference, the methods further involve administering to the subject a first nucleic acid probe coupled to a prodrug of a chemotherapeutic agent and a second nucleic acid probe coupled to an activating agent. The probes hybridize to a first sequence portion and a second sequence portion that are identical in both the wild-type sequence and the mutated sequence. The first and second portions in the wild-type sequence are not within sufficient proximity of each other for the activating agent to convert the prodrug to an active form of the chemotherapeutic agent, thus the chemotherapeutic agent remains inactive and the normal cells remain unharmed. However, in the mutated sequence, the first and second portions are within sufficient proximity of each other for the activating agent to convert the prodrug to an active form of the chemotherapeutic agent, therefore providing targeted delivery of the chemotherapeutic agent to the cancerous or pre-cancerous cell in the subject and killing the cancerous and pre-cancerous cells.

In certain aspects, methods of the invention involve administering a pair of oligonucleotides that are selectively toxic in a cell containing an aneuploidy, e.g., an inversion, a deletion, a loss of heterozygosity, or a genetic rearrangement. In certain embodiments, a first oligonucleotide of the pair has a cytotoxic agent attached and a second oligonucleotide of the pair has an activating agent attached.

DETAILED DESCRIPTION

Many cancers are thought to arise through a series of mutations in genomic DNA, resulting in genomic instability in the form of uncontrolled cellular growth. In normal cells, damage to genomic DNA typically leads to expression of tumor suppressors, such as the cell-cycle regulator, p53. For example, damage to cellular DNA results in increased expression of p53 which arrests the cell cycle to allow repair of the damage. If the damaged DNA cannot be repaired, the cell undergoes apoptosis, thus preventing the accumulation of additional mutations in daughter cells. If however, there is a mutation in the p53 gene itself (or in another cell cycle regulator), damaged cells will proceed through the cell cycle, giving rise to progeny in which additional DNA mutations will go unchecked. It is the accumulation of these mutations that is the hallmark of many cancers.

The invention generally relates to compositions and methods for targeted delivery of chemotherapeutic agents to cancerous and pre-cancerous cells, thereby treating a cancer in a subject. Methods of the invention involve administering probes that hybridize to first and second sequence portions that are identical in wild-type sequences from normal cells and mutated sequences from cancerous cells. A wild-type sequence from a normal cell is that which is most frequently observed in a population and is thus arbitrarily designed the "normal" or "wild-type" sequence.

In contrast, the abnormal or mutant sequence refers to a sequence that displays modifications in sequence and or functional properties (i.e., altered characteristics) when compared to the wild-type sequence. For example, an altered sequence detected in the urine of a patient can display a modification that occurs in DNA sequences from tumor cells and that does not occur in the patient's normal (i.e. non cancerous) cells. It is noted that naturally-occurring mutants can be isolated; these are identified by the fact that they have altered characteristics when compared to the wild-type gene or gene product.

Without limiting the invention to the detection of any specific type of anomaly, mutations can take many forms. A common genetic change characteristic of transformation is loss of heterozygosity. Loss of heterozygosity at a number of tumor suppressor genes has been implicated in tumorigenesis. For example, loss of heterozygosity at the P53 tumor suppressor locus has been correlated with various types of cancer. Ridanpaa, et al., Path. Res. Pract, 191: 399-402 (1995). The loss of the apc and dcc tumor suppressor genes has also been associated with tumor development. Blum, Europ. J. Cancer, 31A: 1369-372 (1995).

Mutations that result loss of genetic material that give rise to cancer, and their location within a gene are known in the art. See, e.g., Hesketh, The Oncogene *Facts Book*, Academic Press Limited (1995). Knowing the mutation and the location of the mutation, one of skill in the art can readily design probes that will hybridize to first and second sequence portions that are identical on both the wild-type and mutant sequence that will flank the mutated region.

Alternatively, samples from the subject may be obtained and sequenced in order to determine the differences between the wild-type sequences from normal cells and the mutant sequences from cancerous and pre-cancerous cells. The sequence data also allows for the determination of the sequence of the first and second portions that flank the mutated region, and this provides information for probe design.

To obtain the wild-type and mutant sequences, a sample is obtained from a subject. The sample may be obtained in any clinically acceptable manner, and the nucleic acids are extracted from the sample by methods known in the art. Generally, nucleic acid can be extracted from a biological sample by a variety of techniques such as those described by Maniatis, et al. (Molecular Cloning: A Laboratory Manual, Cold Spring Harbor, N.Y., pp. 280-281, 1982), the contents of which are incorporated by reference herein in their entirety.

The sample may be a human tissue or bodily fluid. A tissue is a mass of connected cells and/or extracellular matrix material, e.g. skin tissue, nasal passage tissue, CNS tissue, neural tissue, eye tissue, liver tissue, kidney tissue, placental tissue, mammary gland tissue, placental tissue, gastrointestinal tissue, musculoskeletal tissue, genitourinary tissue, bone marrow, and the like, derived from, for example, a human or other mammal and includes the connecting material and the liquid material in association with the cells and/or tissues.

A bodily fluid is a liquid material derived from, for example, a human or other mammal. Such body fluids include, but are not limited to, mucous, blood, plasma, serum, serum derivatives, bile, blood, maternal blood, phlegm, saliva, sweat, amniotic fluid, mammary fluid, urine, and cerebrospinal fluid (CSF), such as lumbar or ventricular CSF. A sample may also be a fine needle aspirate or biopsied tissue. A sample also may be media containing cells or biological material. In certain embodiments, the sample includes nucleic acid molecules that are cell free circulating nucleic acid molecules.

Once obtained, the nucleic acid molecules are sequenced by any method known in the art, e.g., ensemble sequencing or single molecule sequencing. One conventional method to perform sequencing is by chain termination and gel separation, as described by Sanger et al., Proc Natl Acad Sci U S A, 74(12): 5463 67 (1977). Another conventional sequencing method involves chemical degradation of nucleic acid fragments. See, Maxam et al., Proc. Natl. Acad. Sci., 74: 560 564 (1977). Finally, methods have been developed based upon sequencing by hybridization. See, e.g., Drmanac, et al. (Nature Biotech., 16: 54 58, 1998). The contents of each of reference is incorporated by reference herein in its entirety.

In certain embodiments, sequencing is performed by the Sanger sequencing technique. Classical Sanger sequencing involves a single-stranded DNA template, a DNA primer, a DNA polymerase, radioactively or fluorescently labeled nucleotides, and modified nucleotides that terminate DNA strand elongation. If the label is not attached to the dideoxynucleotide terminator (e.g., labeled primer), or is a monochromatic label (e.g., radioisotope), then the DNA sample is divided into four separate sequencing reactions, containing four standard deoxynucleotides (dATP, dGTP, dCTP and dTTP) and the DNA polymerase. To each reaction is added only one of the four dideoxynucleotides (ddATP, ddGTP, ddCTP, or ddTTP). These dideoxynucleotides are the chain-terminating nucleotides, lacking a 3'-OH group required for the formation of a phosphodiester bond between two nucleotides during DNA strand elongation. If each of the dideoxynucleotides carries a different label, however, (e.g., 4 different fluorescent dyes), then all the sequencing reactions can be carried out together without the need for separate reactions.

Incorporation of a dideoxynucleotide into the nascent, i.e., elongating, DNA strand terminates DNA strand extension, resulting in a nested set of DNA fragments of varying length. Newly synthesized and labeled DNA fragments are denatured, and separated by size using gel electrophoresis on a denaturing polyacrylamide-urea gel capable of resolving single-base differences in chain length. If each of the four DNA synthesis reactions was labeled with the same, monochromatic label (e.g., radioisotope), then they are separated in one of four individual, adjacent lanes in the gel, in which each lane in the gel is designated according to the dideoxynucleotide used in the respective reaction, i.e., gel lanes A, T, G, C. If four different labels were utilized, then the reactions can be combined in a single lane on the gel. DNA bands are then visualized by autoradiography or fluorescence, and the DNA sequence can be directly read from the X-ray film or gel image.

The terminal nucleotide base is identified according to the dideoxynucleotide that was added in the reaction resulting in that band or its corresponding direct label. The relative positions of the different bands in the gel are then used to read (from shortest to longest) the DNA sequence as indicated. The Sanger sequencing process can be automated using a DNA sequencer, such as those commercially available from PerkinElmer, Beckman Coulter, Life Technologies, and others.

In other embodiments, sequencing of the nucleic acid is accomplished by a single-molecule sequencing by synthesis technique. Single molecule sequencing is shown for example in Lapidus et al. (U.S. Pat. No. 7,169,560), Quake et al. (U.S. Pat. No. 6,818,395), Harris (U.S. Pat. No. 7,282,337), Quake et al. (U.S. patent application number 2002/0164629), and Braslaysky, et al., PNAS (USA), 100: 3960-3964 (2003), the contents of each of these references is incorporated by reference herein in its entirety. Briefly, a single-stranded nucleic acid (e.g., DNA or cDNA) is hybridized to oligonucleotides attached to a surface of a flow cell. The oligonucleotides may be covalently attached to the surface or various attachments other than covalent linking as known to those of ordinary skill in the art may be employed. Moreover, the attachment may be indirect, e.g., via a polymerase directly or indirectly attached to the surface. The surface may be planar or otherwise, and/or may be porous or non-porous, or any other type of surface known to those of ordinary skill to be suitable for attachment. The nucleic acid is then sequenced by imaging the polymerase-mediated addition of fluorescently-labeled nucleotides incorporated into the growing strand surface oligonucleotide, at single molecule resolution.

Other single molecule sequencing techniques involve detection of pyrophosphate as it is cleaved from incorporation of a single nucleotide into a nascent strand of DNA, as is shown in Rothberg et al. (U.S. Pat. Nos. 7,335,762, 7,264,929, 7,244,559, and 7,211,390) and Leamon et al. (U.S. Pat. No. 7,323,305), the contents of each of which is incorporated by reference herein in its entirety.

In other embodiments, targeted resequencing is used. Resequencing is shown for example in Harris (U.S. patent application numbers 2008/0233575, 2009/0075252, and 2009/0197257), the contents of each of which are incorporated by reference herein in their entirety. Briefly, a specific segment of the target is selected (for example by PCR, microarray, or MIPS) prior to sequencing. A primer designed to hybridize to this particular segment, is introduced and a primer/template duplex is formed. The primer/template duplex is exposed to a polymerase, and at least one detectably labeled nucleotide under conditions sufficient for template dependent nucleotide addition to the primer. The incorporation of the labeled nucleotide is determined, as well the identity of the nucleotide that is complementary to a nucleotide on the template at a position that is opposite the incorporated nucleotide.

After the polymerization reaction, the primer may be removed from the duplex. The primer may be removed by any suitable means, for example by raising the temperature of the surface or substrate such that the duplex is melted, or by changing the buffer conditions to destabilize the duplex, or combination thereof. Methods for melting template/primer duplexes are well known in the art and are described, for example, in chapter 10 of Molecular Cloning, a Laboratory Manual, 3.sup.rd Edition, J. Sambrook, and D. W. Russell, Cold Spring Harbor Press (2001), the teachings of which are incorporated herein by reference.

After removing the primer, the template may be exposed to a second primer capable of hybridizing to the template. In one embodiment, the second primer is capable of hybridizing to the same region of the template as the first primer (also referred to herein as a first region), to form a template/primer duplex. The polymerization reaction is then repeated, thereby resequencing at least a portion of the template.

If the nucleic acid from the sample is degraded or only a minimal amount of nucleic acid can be obtained from the sample, PCR can be performed on the nucleic acid in order to obtain a sufficient amount of nucleic acid for sequencing (See e.g., Mullis et al. U.S. Pat. No. 4,683,195, the contents of which are incorporated by reference herein in its entirety).

Once the wild-type sequences from the normal cells and the mutant sequences from the cancerous or pre-cancerous cells are obtained, these sequences are compared to determine the differences between the sequences. The difference of interest is a loss of genetic material from the wild-type sequence, e.g., a deletion event, that results in the mutant sequence found in the cancerous or pre-cancerous cells.

After determining the region of genetic material that is lost from the wild-type sequence to result in the mutant sequence, the regions of the sequences that flank the mutated region in both the wild-type and mutant sequences (i.e., sequences upstream of the mutated region and downstream of the mutated region) are analyzed. Based on the analysis of the sequences that flank the mutated region, first and second probes are designed to hybridize to first and second sequence portions that flank the mutated region, and that are identical in both the wild-type sequences and the mutant sequences.

Methods of synthesizing oligonucleotide probes are known in the art. See, e.g., Sambrook et al. (DNA microarray: A Molecular Cloning Manual, Cold Spring Harbor, N. Y., 2003) or Maniatis, et al. (Molecular Cloning: A Laboratory Manual, Cold Spring Harbor, N. Y., 1982), the contents of each of which are incorporated by reference herein in their entirety. Suitable methods for synthesizing oligonucleotide probes are also described in Caruthers (Science 230:281-285, 1985), the contents of which are incorporated by reference. The first and second probes each include a nucleotide sequence with substantial complementarity to the first or second regions in the wild-type and mutant sequences, so that the first and second probes hybridize with the first and second portions. Complementarity between probes and the first and second portions need only be sufficient to specifically bind the first and second portions in the wild-type and mutant sequences.

Probes suitable for use in the present invention include those formed from nucleic acids, such as RNA and/or DNA, nucleic acid analogs, locked nucleic acids, modified nucleic acids, and chimeric probes of a mixed class including a nucleic acid with another organic component such as peptide nucleic acids. Probes can be single stranded or double stranded. Exemplary nucleotide analogs include phosphate esters of deoxyadenosine, deoxycytidine, deoxyguanosine, deoxythymidine, adenosine, cytidine, guanosine, and uridine. Other examples of non-natural nucleotides include a xanthine or hypoxanthine; 5-bromouracil, 2-aminopurine, deoxyinosine, or methylated cytosine, such as 5-methylcytosine, and N4-methoxydeoxycytosine. Also included are bases of polynucleotide mimetics, such as methylated nucleic acids, e.g., 2'-O-methRNA, peptide nucleic acids, modified peptide nucleic acids, and any other structural moiety that can act substantially like a nucleotide or base, for example, by exhibiting base-complementarity with one or more bases that occur in DNA or RNA.

The length of the oligonucleotide probe is not critical, as long as the probes are capable of hybridizing to the first and second portions. In fact, probes may be of any length. Probe lengths are based on the analysis of the genetic sequences of the first and second portions that flank the mutated region. For example, probes may be as few as 5 nucleotides, or as much as 5000 nucleotides. Exemplary probes are 5-mers, 10-mers, 15-mers, 20-mers, 25-mers, 50-mers, 100-mers, 200-mers, 500-mers, 1000-mers, 3000-mers, or 5000-mers. Methods for determining an optimal probe length are known in the art. See, e.g., Shuber (U.S. Pat. No. 5,888,778). The first and second probes do not have to be of the same length. In certain embodiments, the first and second probes are the same length, while in other embodiments, the first and second probes are of different lengths.

An activating agent is attached to the first probe, and a prodrug of a chemotherapeutic agent is attached to the second probe. Conjugation of drugs to carrier molecules is shown in (Kramer, et al., J. Biol. Chem., 269:10621, 1994; WO 01/09163; and US 2002/0098999). The attachment can be by covalent linkage. See, Joos et al., Analytical Biochemistry 247:96-101, 1997; Oroskar et al., Clin. Chem. 42:1547-1555, 1996; Khandjian, Mole. Bio. Rep. 11:107-115, 1986; Ekwuribe et al. (U.S. Pat. No. 7,470,663). Exemplary bonding moieties include ester moieties, carbonate moieties, carbamate moieties, amide moieties, epoxide moieties, and secondary amine moieties. An exemplary attachment is direct amine bonding of a terminal nucleotide to an epoxide integrated onto the activating agent or the prodrug of the chemotherapeutic agent. In one embodiment, the prodrug of the chemotherapeutic agent and the activating agent are modified to include an epoxide, e.g., a epoxy silane. Probes may be directly or indirectly linked to an epoxide. In a direct attachment embodiment, the epoxide is introduced to a nucleic acid bearing an amine group. In another embodiment, terminal transferase is used to add an amine-terminated nucleotide to a nucleic acid to be attached to the epoxide.

The bonding also can be through non-covalent linkage. See, e.g., Ekwuribe et al. (U.S. Pat. No. 7,470,663). For example, biotin-streptavidin (Taylor et al., J. Phys. D. Appl. Phys. 24:1443, 1991) and digoxigenin with anti-digoxigenin (Smith et al., Science 253:1122, 1992). When biotin-streptavidin linkage is used, the nucleic acids can be biotinylated, while the prodrug of the chemotherapeutic agent and the activating agent can be modified with streptavidin. Other examples of linkers include antigen/antibody, digoxigenin/anti-digoxigenin, dinitrophenol, fluorescein, and other haptens known in the art.

The same attachment chemistry may be used to link the activating agent to the first probe and the prodrug of the chemotherapeutic agent to the second probe. Alternatively, different attachment chemistry may be used to link the activating agent to the first probe and the prodrug of the chemotherapeutic agent to the second probe.

Chemotherapeutic agents are known in the art, and methods of the invention may use any chemotherapeutic agent. See e.g., The *Merck Index* (14$^{th}$ edition. Whitehouse Station, N.J., 2009) or Don et al. (Cancer Chemotherapy Handbook, 2d edition, pages 15-34, Appleton & Lange, Connecticut, 1994). The chemotherapeutic agent to be administered is chosen by one of skill in the art based upon may factors, such as type of cancer, stage of the cancer, aggressiveness of the cancer, traits of the patient (e.g., age, allergies, medical history, etc.). Examples of chemotherapeutic agents include: altretamine, asparaginase, bleomycin, capecitabine, carboplatin, carmustine, cladribine, cisplatin, cyclophosphamide, cytarabine, dacarbazine, actinomycin D, docetaxel, doxorubicin, imatinib, etoposide, fludarabine, fluorouracil, gemcitabine, hydroxyurea, idarubicin, ifosfamide, irinotecan, methotrexate, mitomycin, mitotane, mitoxantrone, paclitaxel, topotecan, vinblastine, vincristine, and vinorelbine.

The activating agent refers to an agent that causes transformation of the prodrug of the chemotherapeutic agent to an active form of the chemotherapeutic agent. The activating agent is chosen based upon the prodrug of the chemotherapeutic agent, i.e., the activating agent is chosen to be compatible with the prodrug of the chemotherapeutic agent such that the activating agent converts the prodrug to an active form of the chemotherapeutic agent. Exemplary activating agents include a chemically conjugated antibody fragment, a metabolizing enzyme, and a catalytic antibody.

Upon administration of the probes to a subject, the first and second probes hybridize to the first and second portions of the sequences in the normal cells and in the cancerous or pre-cancerous cells. For the wild-type sequences, the first and second portions are not within sufficient proximity of each other for the activating agent to convert the prodrug to an active form of the chemotherapeutic agent. Thus the chemotherapeutic agent remains inactive and the normal cell is unharmed.

However, the sequences in the cancerous or pre-cancerous cells have undergone the mutation event resulting in loss of genetic material between the first and second portions. Thus in the mutated sequences, the first and second portions are within sufficient proximity of each other for the activating agent to convert the prodrug to an active form of the chemotherapeutic agent, thereby providing targeted delivery of the chemotherapeutic agent to the cancerous or pre-cancerous cell in the subject, and killing those cells.

In certain embodiments, the first and second sequence portions are adjacent to each other in the mutated sequence. Alternatively, the first and second portions are a certain distance apart in the mutant sequences. The distance separating the first and second sequence portions in the mutated sequence is based upon where the probes have been designed to hybridize to the mutant sequences. In certain embodiments, the first and second portions are separated by about 5 nucleotides in the mutated sequence, by about 10 nucleotides, by about 20 nucleotides, by about 50 nucleotides, by about 100 nucleotides, by about 200 nucleotides, by about 500 nucleotides, by about 1000 nucleotides, by about 2000 nucleotides, by about 5000 nucleotides, by about 10,000 nucleotides, by about 50,000 nucleotides, by about 100,000 nucleotides, etc. The distance between the first and second sequence portions is only limited by the interaction of the activating agent and the prodrug of the chemotherapeutic agent. The first and second probes must hybridize close enough to each other on the mutant sequence such that the activating agent is capable of converting the prodrug to an active form.

The compositions, according to the method of the present invention, may be administered using any amount and any route of administration effective for treating the cancer. Thus, the expression "amount effective for treating a cancer", as used herein, refers to a sufficient amount of composition to beneficially prevent or ameliorate the symptoms of the cancer.

The exact dosage is chosen by the individual physician in view of the patient to be treated. Dosage and administration are adjusted to provide sufficient levels of the chemotherapeutic agent or to maintain the desired effect. Additional factors which may be taken into account include the severity of the disease state, age, weight and gender of the patient; diet, time and frequency of administration; route of administration; drug combinations; reaction sensitivities; and tolerance/response to therapy. Long acting pharmaceutical compositions might be administered hourly, twice hourly, every 3 to four hours, daily, twice daily, every 3 to 4 days, every week, or once every two weeks depending on half-life and clearance rate of the particular composition.

The chemotherapeutic agents of the invention are preferably formulated in dosage unit form for ease of administration and uniformity of dosage. The expression "dosage unit form" as used herein refers to a physically discrete unit of active agent appropriate for the patient to be treated. It will be understood, however, that the total daily usage of the compositions of the present invention will be decided by the attending physician within the scope of sound medical judgment. For any active agent, the therapeutically effective dose can be estimated initially either in cell culture assays or in animal models, as provided herein, usually mice, but also potentially from rats, rabbits, dogs, or pigs. The animal cell model provided herein is also used to achieve a desirable concentration and total dosing range and route of administration. Such information can then be used to determine useful doses and routes for administration in humans.

A therapeutically effective dose refers to that amount of chemotherapeutic agent that ameliorates the symptoms or condition or prevents progression of the cancer. Therapeutic efficacy and toxicity of active agents can be determined by standard pharmaceutical procedures in cell cultures or experimental animals. For example, therapeutic efficacy and toxicity can be determined by minimal efficacious dose or NOAEL (no observable adverse effect level). Alternatively, an ED50 (the dose is therapeutically effective in 50% of the population) and LD50 (the dose is lethal to 50% of the population) can be determined in cell cultures or experimental animals. The dose ratio of toxic to therapeutic effects is the therapeutic index, and it can be expressed as the ratio, LD50/ED50. Pharmaceutical compositions that exhibit large therapeutic indices are preferred.

The daily dosage of the products may be varied over a wide range, such as from 0.001 to 100 mg per adult human per day. A unit dose typically contains from about 0.001 micrograms to about 500 micrograms of the chemotherapeutic agent, preferably from about 0.1 micrograms to about 100 micrograms of chemotherapeutic agent, more preferably from about 1.0 micrograms to about 10 micrograms of chemotherapeutic agent. An effective amount of the drug is ordinarily supplied at a dosage level of from about 0.0001 mg/kg to about 25 mg/kg of body weight per day. For example, the range is from about 0.001 to 10 mg/kg of body weight per day, or from about 0.001 mg/kg to 1 mg/kg of body weight per day. The compositions may be administered on a regimen of, for example, one to four or more times per day.

As formulated with an appropriate pharmaceutically acceptable carrier in a desired dosage, the pharmaceutical composition provided herein is administered to humans and other mammals topically such as ocularly, nasally, bucally, orally, rectally, parenterally, intracisternally, intravaginally, or intraperitoneally.

As used herein, the term "pharmaceutically acceptable carrier" includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences Ed. by Gennaro, Mack Publishing, Easton, Pa., 1995 provides various carriers used in formulating pharmaceutical compositions and known techniques for the preparation thereof. Some examples of materials which can serve as pharmaceutically acceptable carriers include, but are not limited to, sugars such as glucose and sucrose; excipients such as cocoa butter and suppository waxes; oils such as peanut oil, cottonseed oil, safflower oil, sesame oil, olive oil, corn oil, and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, preservatives and antioxidants can also be present in the composition, according to the judgment of the formulator.

Liquid dosage forms for ocular, oral, or other systemic administration include, but are not limited to, pharmaceutically acceptable emulsions, microemulsions, solutions, suspensions, syrups and elixirs. In addition to the active agent(s), the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the ocular, oral, or other systemically-delivered compositions can also include adjuvants such as wetting agents, and emulsifying and suspending agents.

Dosage forms for topical or transdermal administration of an inventive pharmaceutical composition include ointments, pastes, creams, lotions, gels, powders, solutions, sprays, inhalants, or patches. The active agent is admixed under sterile conditions with a pharmaceutically acceptable carrier and any needed preservatives or buffers as may be required. For example, ocular or cutaneous routes of administration are achieved with aqueous drops, a mist, an emulsion, or a cream. Administration may be therapeutic or it may be prophylactic. The invention includes ophthalmological devices, surgical devices, audiological devices or products which contain disclosed compositions (e.g., gauze bandages or strips), and methods of making or using such devices or products. These devices may be coated with, impregnated with, bonded to or otherwise treated with a composition as described herein.

Transdermal patches have the added advantage of providing controlled delivery of the active ingredients to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. In order to prolong the effect of an active agent, it is often desirable to slow the absorption of the agent from subcutaneous or intramuscular injection. Delayed absorption of a parenterally administered active agent may be accomplished by dissolving or suspending the agent in an oil vehicle. Injectable depot forms are made by forming microencapsule matrices of the agent in biodegradable polymers such as polylactide-polyglycolide. Depending upon the ratio of active agent to polymer and the nature of the particular polymer employed, the rate of active agent release can be controlled. Examples of other biodegradable polymers include poly(orthoesters) and poly(anhydrides). Depot injectable formulations are also prepared by entrapping the agent in liposomes or microemulsions which are compatible with body tissues.

Compositions for rectal or vaginal administration are preferably suppositories which can be prepared by mixing the active agent(s) of this invention with suitable non-irritating excipients or carriers such as cocoa butter, polyethylene glycol or a suppository wax which are solid at ambient temperature but liquid at body temperature and therefore melt in the rectum or vaginal cavity and release the active agent(s).

Solid dosage forms for oral administration include capsules, tablets, pills, powders, and granules. In such solid dosage forms, the active agent is mixed with at least one inert, pharmaceutically acceptable excipient or carrier such as sodium citrate or dicalcium phosphate and/or a) fillers or extenders such as starches, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof.

Solid compositions of a similar type may also be employed as fillers in soft and hard-filled gelatin capsules using such excipients as milk sugar as well as high molecular weight polyethylene glycols and the like. The solid dosage forms of tablets, dragees, capsules, pills, and granules can be prepared with coatings and shells such as enteric coatings, release controlling coatings and other coatings well known in the pharmaceutical formulating art. In such solid dosage forms the active agent(s) may be admixed with at least one inert diluent such as sucrose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain pacifying agents and can also be of a composition that they release the active agent(s) only, or preferentially, in a certain part of the intestinal tract, optionally, in a delayed manner. Examples of embedding compositions which can be used include polymeric substances and waxes.

INCORPORATION BY REFERENCE

References and citations to other documents, such as patents, patent applications, patent publications, journals, books, and papers have been made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method for treating a cancer in a subject, the method comprising:
   sequencing a nucleic acid found in a normal cell of a subject, thereby obtaining a wild-type sequence;
   sequencing a nucleic acid found in a cancerous or pre-cancerous cell of the subject, thereby obtaining a mutated sequence;
   comparing the wild-type sequence and the mutated sequence, thereby determining a difference between the wild-type sequence and the mutated sequence;
   administering to the subject a first nucleic acid probe coupled to a prodrug of a chemotherapeutic agent and a second nucleic acid probe coupled to an activating agent; wherein the probes hybridize to a first portion and a second portion that are identical in both the wild-type sequence and the mutated sequence;
   wherein the first and second portions in the wild-type sequence are not within sufficient proximity of each other for the activating agent to convert the prodrug to an active form of the chemotherapeutic agent; and
   wherein the first and second portions in the mutated sequence are within sufficient proximity of each other for the activating agent to convert the prodrug to an active form of the chemotherapeutic agent, thereby providing targeted delivery of the chemotherapeutic agent to the cancerous or pre-cancerous cell in the subject.

2. The method according to claim 1, wherein sequencing is by a single molecule sequencing-by-synthesis technique.

3. The method according to claim 1, further comprising synthesizing the first and second nucleic acid probes.

4. The method according to claim 1, further comprising coupling the prodrug to the first nucleic acid probe and coupling the activating agent to the second nucleic acid probe.

5. The method according to either of claim 1, wherein sequencing is sequencing-by-synthesis.

6. The method according to claim 1, wherein the cancer is selected from the group consisting of: brain, bladder, blood, bone, breast, cervical, colorectal, gastrointestinal, endocrine, kidney, liver, lung, ovarian, pancreatic, prostate, and thyroid.

7. The method according to claim 1, wherein the cytotoxic agent is selected from the group consisting of: altretamine, asparaginase, bleomycin, capecitabine, carboplatin, carmustine, cladribine, cisplatin, cyclophosphamide, cytarabine, dacarbazine, actinomycin D, docetaxel, doxorubicin, imatinib, etoposide, fludarabine, fluorouracil, gemcitabine, hydroxyurea, idarubicin, ifosfamide, irinotecan, methotrexate, mitomycin, mitotane, mitoxantrone, paclitaxel, topotecan, vinblastine, vincristine, and vinorelbine.

8. The method according to claim 1, wherein the probes are DNA probes.

9. The method according to claim 1, wherein the first and second probes are administered in the same formulation.

10. The method according to claim 1, wherein the administering of the first and second probe is separate.

11. The method according to claim 1, wherein the activating agent is selected from the group consisting of: a chemically conjugated antibody fragment, a metabolizing enzyme, and a catalytic antibody.

12. The method according to claim 1, wherein the first and second probes are each a 15-mer.

13. The method according to claim 1, wherein the first and second probes hybridize adjacent to each other on the mutated sequence.

14. The method according to claim 1, wherein the first and second probes hybridize to the mutated sequence with a region of the mutated sequence remaining between the first and second probes.

* * * * *

(12) EX PARTE REEXAMINATION CERTIFICATE (10806th)
United States Patent
Shuber

(10) Number: US 8,575,124 C1
(45) Certificate Issued: Feb. 2, 2016

(54) COMPOSITIONS AND METHODS FOR TREATING CANCER

(76) Inventor: Anthony P. Shuber, Mendon, MA (US)

Reexamination Request:
No. 90/013,266, Jun. 10, 2014

Reexamination Certificate for:
Patent No.: 8,575,124
Issued: Nov. 5, 2013
Appl. No.: 13/030,989
Filed: Feb. 18, 2011

Related U.S. Application Data

(60) Provisional application No. 61/305,836, filed on Feb. 18, 2010.

(51) Int. Cl.
*C12N 15/11* (2006.01)
*C07H 21/04* (2006.01)
*A61K 47/48* (2006.01)
*A61K 38/50* (2006.01)
*A61K 38/43* (2006.01)
*A61K 45/06* (2006.01)
*C12Q 1/68* (2006.01)
*A61K 39/395* (2006.01)

(52) U.S. Cl.
CPC ............ *A61K 47/4813* (2013.01); *A61K 38/43* (2013.01); *A61K 38/50* (2013.01); *A61K 39/395* (2013.01); *A61K 45/06* (2013.01); *A61K 47/48092* (2013.01); *C12Q 1/6881* (2013.01)

(58) Field of Classification Search
None
See application file for complete search history.

(56) References Cited

To view the complete listing of prior art documents cited during the proceeding for Reexamination Control Number 90/013,266, please refer to the USPTO's public Patent Application Information Retrieval (PAIR) system under the Display References tab.

*Primary Examiner* — Shri Ponnaluri

(57) ABSTRACT

This invention generally relates to compositions and methods for targeted delivery of chemotherapeutic agents to cancerous and pre-cancerous cells, thereby treating a cancer in a subject.

EX PARTE REEXAMINATION CERTIFICATE

THE PATENT IS HEREBY AMENDED AS INDICATED BELOW.

AS A RESULT OF REEXAMINATION, IT HAS BEEN DETERMINED THAT:

Claims 1-14 are cancelled.

\* \* \* \* \*